US006531571B1

(12) United States Patent
Gray

(10) Patent No.: US 6,531,571 B1
(45) Date of Patent: Mar. 11, 2003

(54) METHOD FOR THE REMOVAL OF EXCESS AMOUNTS OF WATER-SOLUBLE AMINES FROM MANNICH CONDENSATION PRODUCTS

(75) Inventor: James A. Gray, Novato, CA (US)

(73) Assignee: Chevron Oronite Company LLC, San Ramon, CA (US)

( * ) Notice: Subject to any disclaimer, the term of this patent is extended or adjusted under 35 U.S.C. 154(b) by 297 days.

(21) Appl. No.: 09/676,406

(22) Filed: Sep. 29, 2000

(51) Int. Cl.[7] .................................................. C08F 6/00
(52) U.S. Cl. ....................................................... 528/502
(58) Field of Search .......................................... 528/502

(56) References Cited

U.S. PATENT DOCUMENTS

| 3,368,972 A | 2/1968 | Otto ........................... 252/47.5 |
| 3,798,247 A | 3/1974 | Piasek et al. ............. 260/404.5 |
| 4,231,759 A | 11/1980 | Udelhofen et al. ............. 44/75 |
| 4,334,085 A | 6/1982 | Basalay et al. ............. 564/367 |
| 4,507,475 A | 3/1985 | Straehle et al. ............. 536/120 |
| 4,528,364 A | 7/1985 | Prier ........................... 528/370 |
| 5,003,111 A | 3/1991 | Harper ....................... 568/618 |
| 5,055,496 A | 10/1991 | Harper ....................... 521/174 |
| 5,300,701 A | 4/1994 | Cherpeck ..................... 568/792 |
| 5,399,178 A | 3/1995 | Cherpeck ..................... 44/415 |
| 5,413,614 A | 5/1995 | Cherpeck ..................... 44/387 |
| 5,482,522 A | 1/1996 | Cherpeck ..................... 44/391 |
| 5,483,523 A | 1/1996 | Nederlof ..................... 370/58.3 |
| 5,876,468 A | 3/1999 | Moreton ...................... 44/415 |

FOREIGN PATENT DOCUMENTS

| JP | 3-195728 | 8/1991 |
| JP | 4-197407 | 7/1992 |
| JP | 9-176073 | 7/1997 |

*Primary Examiner*—Terressa M. Boykin
(74) *Attorney, Agent, or Firm*—S. G. K. Lee

(57) ABSTRACT

The present invention provides a method for removing excess amounts of water-soluble amines from a diluted crude Mannich condensation product containing about 40 to 80 weight percent crude Mannich condensation product in an inert solvent which comprises:

a) filtering the diluted crude Mannich condensation product in the presence of magnesium silicate and water, and in the further presence of a filter aid when the particle size distribution of the magnesium silicate is such that the average particle size is below about 50 microns; and b) recovering a filtrate containing a Mannich condensation product having less than about 0.05 mEq/g of water-soluble amine.

9 Claims, No Drawings

METHOD FOR THE REMOVAL OF EXCESS AMOUNTS OF WATER-SOLUBLE AMINES FROM MANNICH CONDENSATION PRODUCTS

BACKGROUND OF THE INVENTION

1. Field of the Invention

The present invention relates to a method for the removal of excess amounts of water-soluble amines from Mannich condensation products thereby improving the formulation properties of the Mannich product. More particularly, the present invention relates to removing excess amounts of water-soluble amines from Mannich condensation products to levels below about $0.05 \times 10^{-3}$ equivalents of amine per gram of Mannich product (0.05 mEq/g) by filtering the Mannich condensation product with a solid filtering agent having an active surface.

2. Description of the Related Art

Mannich condensation products as fuel and lubricating oil additives are well known in the art and have been widely documented in the patent literature; e.g., U.S. Pat. Nos. 3,368,972; 3,798,247; 4,231,759; 5,399,178; 5,413,614; 5,482,522; and 5,483,523. As fuel additives, Mannich condensation products are particularly effective for the prevention and control of engine deposits, particularly engine intake system deposits, such as intake valve deposits. These additives are based upon the condensation products of a hydroxyaromatic compound, an amine, and an aldehyde.

For example, U.S. Pat. No. 4,231,759 to Udelhofen and Watson discloses reaction products obtained by the Mannich condensation of a high molecular weight alkyl-substituted hydroxyaromatic compound, an amine containing an amino group having at least one active hydrogen atom, and an aldehyde, such as formaldehyde. This patent further teaches that such Mannich condensation products are useful detergent additives in fuels for the control of deposits on carburetor surfaces and intake valves.

The foregoing Mannich condensation products are commonly prepared by the conventional technique of adding the aliphatic aldehyde to a heated mixture of the hydroxyaromatic compound and amine reagents, and then heating the resultant mixture to a temperature between 35° to 180° C. until dehydration is complete. The reaction may be done in the presence or absence of a solvent. Typical solvents include benzene, toluene, xylene, methanol, and other commercially available aromatic or aliphatic solvents. Light mineral oils and base oils such as those used in blending stocks to prepare lubricating oil formulations in which the product is formed as an oil concentrate are also used. The water byproduct is removed by heating the reaction mixture to a temperature sufficiently high, at least during the last part of the process, to drive off the water. The water may come off alone, or as an azeotrope mixture with the solvent, usually with the aid of vacuum or an inert stripping gas like nitrogen.

U.S. Pat. No. 3,798,247 to Piasek and Karll teaches that the reaction under Mannich condensation conditions, like other chemical reactions, does not go to theoretical completion and some portion of the reactants, generally the amine, remains unreacted or only partially reacted as a coproduct. Unpurified products of Mannich processes also commonly contain small amounts of insoluble particle byproducts of the Mannich condensation reaction that appear to be the high molecular weight condensation product of formaldehyde and polyamines. The amine and amine byproducts lead to haze formation during storage and, in diesel lubricating oil formulations, to rapid buildup of diesel engine piston ring groove carbonaceous deposits and skirt varnish. The insoluble or borderline soluble byproducts are substantially incapable of removal by filtration and severely restrict product filtration rate. These drawbacks were overcome by adding long-chain carboxylic acids to reduce the amount of solids formation from the Mannich reaction by rendering the particulate polyamine-formaldehyde condensation product soluble through formation of amide-type links. In particular, oleic acid worked well at 0.1 to 0.3 mole/mole of alkylphenol. The quantity of unconsumed or partially reacted amine was not mentioned in the patent.

U.S. Pat. No. 4,334,085 to Basalay and Udelhofen discloses that Mannich condensation products can undergo transamination, and this is seen as a solution to the problem of byproduct amine-formaldehyde resin formation encountered by Piasek and Karll in U.S. Pat. No. 3,798,247, above, eliminating the need for using a fatty acid. Basalay and Udelhofen defined transamination as the reaction of a Mannich adduct based on a single-nitrogen amine with a polyamine to exchange the polyamine for the single-nitrogen amine. The examples in this patent suggest that the unconsumed amine and partially reacted amine discussed in U.S. Pat. No. 3,798,247 are not merely unconsumed, but must be in chemical equilibrium with the product of the Mannich condensation reaction. In Example 1 of U.S. Pat. No. 4,334,085, a Mannich condensation product is made from 0.5 moles of polyisobutylphenol, 1.0 mole of diethylamine and 1.1 moles of formaldehyde. To 0.05 moles of this product was added 0.05 moles of tetraethylenepentamine (TEPA) and then the mixture was heated to 155° C. while blowing with nitrogen. The TEPA replaced 80 to 95% of the diethylamine in the Mannich product as the nitrogen stripped off the small amount of diethylamine made available by the equilibrium with the Mannich product.

In fuel additive applications, the presence of small amounts of low molecular weight amine in dispersant components such as the Mannich condensation product can lead to formulation incompatibilities (for example, with certain corrosion inhibitors or demulsifiers) and air sensitivity (for example, reaction with carbon dioxide in the air). For example, corrosion inhibitors are typically organic acids. These can react with excess amounts of low molecular weight amines in the Mannich component at room temperature to form insoluble salts and at higher temperatures to form insoluble amides. Incompatibility or air sensitivity is manifested by formation of haze, floc, solids, and or gel in the formulation over time. The incompatibility may occur in the absence of air. Consequently, the manufacturing process for amine dispersant-type fuel additives must include a step to remove low molecular weight amines to low levels. However, in view of the unique chemistry of Mannich condensation products, an effective purification step may not be readily accomplished. In particular, the chemical equilibrium can generate additional low molecular weight amines if the product is heated too much during the purification step. Therefore, there is a need for an economical process to reduce the unconsumed amine and the amine-formaldehyde intermediate to a low level after the Mannich reaction.

There are a number of methods that may be used for removing excess amine after a Mannich condensation reaction. Some possible approaches include washing with water, distillation, and absorption/filtration. However, these techniques must be applied with great care because the chemical equilibrium of the Mannich condensation product has the potential to release more amine during the purification process.

In the area of fuel additives, a typical way of determining the efficiency of the purification step is to measure the low molecular weight amine content of the Mannich product before and after the purification step. The Mannich sample is diluted with solvent and then extracted with water. Analysis of the water extract by gas chromatography or titration yields the amount of water-soluble amine either in weight percent by gas chromatography or milliequivalents of base per gram of Mannich product by titration (mEq/g).

Water washing and simple vacuum distillation are well known techniques for removing water-soluble amines in fuel additive manufacturing processes. Water washing is very complex and relatively costly to implement on a commercial scale. This approach requires multiple washes, and there are recycle streams needed for the solvents that promote phase separation. Fuel additives are good dispersants by nature, and so contacting with water and phase separation become major technical problems.

Simple vacuum distillation is practically limited to amines with normal boiling points well below 200° C. For example, U.S. Pat. No. 5,876,468 to Moreton uses a distillation temperature of 80° C. for an ethylenediamine-derived Mannich product, but does not give specific temperatures for several other higher boiling amines such as diethylenetriamine or triethylenetetramine. This patent does not disclose any information on water-soluble amine content of the Mannich products in the examples. Also, the Moreton patent does not mention any problem with formulation incompatibilities even though one would expect a problem with some of the higher boiling amines, such as triethylenetetramine, in the formulation used for the diesel engine test in this patent.

The Mannich product made from diethylenetriamine (DETA) presents a typical situation. DETA has a boiling point of about 207° C. and is difficult to remove to low levels without water washing. In theory, distillation could be used to remove DETA, but due to its low volatility this requires a very specialized fractionation column with high turnover that operates in tandem with the reactor and results in a solvent byproduct containing DETA and DETA-formaldehyde compounds that must be recycled. This creates another procedure for waste product handling that is often undesirable due to the added complexity and expense in manufacturing the product.

There appears to be no mention in the available Mannich patent literature of the use of solid absorbents combined with filtration to remove low molecular weight amines from Mannich condensation products. However, in the field of polyols, solid absorbents have been used successfully to remove alkaline metal catalyst from the polyols after synthesis.

Thus, the removal of alkaline catalysts from various polyether polyols is also known in the art. For example, U.S. Pat. No. 4,528,364 to Prier discloses a method of removing alkaline catalysts from polyether polyols and polyalkylene carbonate polyols which comprises dissolving the polyol in an aprotic solvent and then contacting the polyol solution with a sufficient amount of an adsorbent to adsorb the alkaline catalysts, followed by physically separating the adsorbent from the polyol solution. This patent teaches that the process described therein is advantageous, as there is no water present to hydrolyze either the polyether polyol or the polyalkylene carbonate polyol. This patent further teaches that preferred adsorbents are aluminum and alkaline earth metal silicates, with magnesium silicate being most preferred. Suitable catalysts taught by this patent include alkali metal borates, alkaline earth metal borates, and ammonium borates.

U.S. Pat. No. 4,507,475 to Straehle et al. discloses a process for purifying crude polyether polyols prepared by anionic polymerization of alkylene oxides in the presence of basic catalysts, wherein the polyols are mixed with water and ortho-phosphoric acid in certain quantity ratios, an adsorption agent is incorporated in the reaction mixture, the mixture is filtered, and the water is removed from the polyol by distillation. This patent teaches that the polyol is mixed with 0.2 to 1.5 parts by weight of water per 100 parts of polyol and that the water content is of decisive importance for the quality of the purification. This patent further teaches that commonly used catalysts are alkali alkoxides and alkali hydroxides, preferably potassium hydroxide. Preferred adsorption agents taught by this patent are natural and synthetic silicas of earth alkali metals or aluminum, preferably synthetic magnesium silicate. This patent also teaches that it is advantageous to use filtration aids such as perlite, kieselguhr and diatomaceous earth, in addition to the adsorption agents.

U.S. Pat. Nos. 5,003,111 and 5,055,496, both to Harper, disclose a process for preparing polyether polyols by polymerizing isobutylene oxide with other alkylene oxides in the presence of an alkali metal catalyst and a crown ether cocatalyst to afford polyols containing low levels of unsaturation. These patents teach that the alkali metal may be derived from any suitable source, including alkali metal hydroxides, alkoxides and phenoxides, and that the alkali metal is preferably potassium or sodium. These patents further teach that the crude polyether polyol is treated to separate the alkali metal and crown ether from the product and that contacting the crude polyol with an adsorption agent, such as magnesium silicate, effectively reduces the alkali metal and crown ether content to acceptable levels. In the examples, these patents teach that the crude polyol was treated with 4% magnesium silicate, 0.5% water, and 1% diatomaceous earth for four hours at 110° C. to remove potassium hydroxide and crown ether. The polyol was then filtered through diatomaceous earth, diluted with toluene, water washed, and vacuum stripped to provide the final polyol.

Japanese Kokai (laid-open) Patent Application No. HEI 3-195728 (1991) discloses a process for the purification of polyoxyalkylene polyol which has been synthesized in the presence of alkaline catalyst, which involves neutralizing the crude polyol with mineral acid to a pH of 4.5 to 7.5, followed by adsorption with a synthetic magnesium silicate containing less than 0.5 weight percent sodium, wherein the amount of synthetic magnesium silicate used as adsorbent is 0.05 to 5 weight percent of the polyol. The catalysts used in the polyol synthesis are described as potassium hydroxide, sodium hydroxide, potassium alcoholate, sodium alcoholate, potassium carbonate, sodium carbonate, metallic potassium, and metallic sodium.

Japanese Kokai (laid-open) Patent Application No. HEI 4-197407 (1992) discloses a process for the purification of polyethers, in which catalyst is removed from crude polyethers having a high viscosity, which involves an adsorption treatment performed by the addition of a magnesium silicate adsorbent having an average particle diameter of above 100 micrometers to the crude polyether product, followed by filtration through a filter precoated with a filter aid consisting of diatomaceous earth having an average particle diameter of more than 100 micrometers. Catalysts disclosed for use in the synthesis of the crude polyethers include alkaline catalysts, such as potassium hydroxide and sodium hydroxide, and complex metal cyano compounds, such as zinc hexacyano cobaltate complex and zinc hexacyano iron complex. The complex metal cyano compounds are preferred for making polyether polyols of 8,000 to 50,000 molecular weight.

Japanese Kokai (laid-open) Patent Application No. HEI 9-176073 (1997) discloses a process for manufacturing a propenyl ether compound in which an allyl ether compound is subjected to a rearrangement reaction with the use of an alkali metal hydroxide and/or alkaline earth metal hydroxide as a catalyst, wherein a silicate type adsorbent is used for catalyst removal and purification. This publication teaches that the adsorbent may be selected from acid clay, zeolite, synthetic magnesium silicate, synthetic aluminosilicate, and synthetic magnesium aluminosilicate. This publication further teaches that improved efficiency of catalyst removal can be obtained by the addition of water during the catalyst removal and purification period, wherein the weight ratio of water to silicate adsorbent is from 20:100 to 500:100.

Accordingly, there is a need in the art to have a simple and cost-effective process whereby low molecular weight amines, such as DETA and DETA-formaldehyde intermediates, can be removed from Mannich condensation products. Removing such amines to levels below about 0.05 mEq/g makes the Mannich condensation product compatible with other components used to formulate fuel additive packages, such as organic acids, and eliminates formulation air sensitivity due to carbon dioxide reaction with the low molecular weight amines.

The present invention provides a process which eliminates the problems associated with excess water-soluble amine levels above about 0.05 mEq/g, while avoiding the need for extensive water washing and specialized fractionation columns.

SUMMARY OF THE INVENTION

The present invention provides a method for removing excess amounts of water-soluble amines from a diluted crude Mannich condensation product containing about 40 to 80 weight percent crude Mannich condensation product in an inert solvent, which comprises:

a) filtering the diluted crude Mannich condensation product in the presence of about 90 to 230 g of magnesium silicate per equivalent of water-soluble amine in the diluted crude Mannich condensation product and about 20 to 150 g of water per equivalent of water-soluble amine in the diluted crude Mannich condensation product, and in the further presence of about 0.1 to 2%, based on the diluted crude Mannich condensation product, of a filter aid when the particle size distribution of the magnesium silicate is such that the average particle size is below about 50 microns; and b) recovering a filtrate containing a Mannich condensation product having less than about 0.05 mEq/g of water-soluble amine.

In the present invention the Mannich condensation product is a product of (1) a high molecular weight alkyl-substituted hydroxyaromatic compound wherein the alkyl group has a number average molecular weight of from about 300 to 5,000 (2) an amine which contains an amino group having at least one active hydrogen atom, and (3) an aldehyde, wherein the respective molar ratio of reactants (1), (2) and (3) is 1:0.1–10:0.1–10. Preferred polyalkyl hydroxyaromatic compounds used for the Mannich condensation reaction include polypropyl phenol and polybutyl phenol, especially polyisobutyl phenol.

In the present invention, the crude Mannich condensation product is preferably diluted with inert solvent to give a Mannich condensation product concentration in the range of about 50 to 80 weight percent, more preferably about 60 to 75 weight percent, and most preferably about 65 to 70 weight percent. When utilized, the preferred filter aid employed in the present method is diatomaceous earth.

The magnesium silicate is present at a concentration of about 90 to 230 g per equivalent of water-soluble amine in the diluted crude Mannich condensation product and the filter aid is present at a concentration of about 0 to 2 weight percent, based on the diluted crude Mannich condensation product. The filter aid employed in the present invention is preferably diatomaceous earth.

The water employed in the present invention is present during filtration at a concentration of about 20 to 150 g per equivalent of water-soluble amine in the diluted crude Mannich condensation product. Preferably the water used is deionized water. The filtration is carried out at a temperature in the range of about 40° C. to 95° C.

Among other factors, the present invention is based on the discovery that excess amounts of water-soluble amines can be effectively removed from Mannich condensation products to levels below about 0.05 mEq/g, preferably below 0.04 mEq/g, by filtering the Mannich condensation product with a solid filtering agent having an active surface. This is particularly surprising since conventional filtration technology can only approach 0.05 mEq/g with the use of large amounts of diatomaceous earth which results in a large amount of valuable product lost in the filter cake and high solid waste disposal costs. In addition, with conventional filtration techniques the filtrate is very hazy because the diatomaceous earth absorbs only a small amount of the water needed to facilitate the adsorption of water-soluble amines. The present purification method also solves a major problem in formulating the Mannich condensation product. Excess amounts of water-soluble amines above 0.05 mEq/g can cause incompatibilities with other components used to formulate fuel additive packages, such as corrosion inhibitors and demulsifiers, and can make the formulation sensitive to air exposure. The incompatibility with other components manifests itself in the formation of insoluble material, haze, flocs, and sediment. Air sensitivity will give similar symptoms.

DETAILED DESCRIPTION OF THE INVENTION

The present invention involves a method for removing excess amounts of water-soluble amines, primarily low molecular weight amines and their derivatives, from Mannich condensation products. The method of the present invention involves filtration of the Mannich condensation product through a solid filtering agent having an active surface to remove the excess amounts of water-soluble amines. The resulting filtrate contains a Mannich condensation product having less than about 0.05 mEq/g of water-soluble amines, resulting in a product with improved compatibility with other components when used in fuel additive compositions. The present invention will now be described in more detail hereinbelow.

The Mannich Condensation Product

Typically, Mannich reaction products useful in the present invention are obtained by condensing an alkyl-substituted hydroxyaromatic compound whose alkyl-substituent has a number average molecular weight of from about 300 to 5,000, preferably polyalkylphenol whose polyalkyl substituent is derived from 1-mono-olefin polymers having a number average molecular weight of from about 300 to 5,000, more preferably from about 400 to 3,000; an amine containing at least one >NH group, preferably an alkylene polyamine of the formula:

wherein A is a divalent alkylene radical having about 1 to 10 carbon atoms and x is an integer from about 1 to 10; and an aldehyde, preferably formaldehyde or paraformaldehyde, in the presence of a solvent.

High molecular weight Mannich reaction products useful as additives in fuel additive compositions are preferably prepared according to conventional methods employed for the preparation of Mannich condensation products, using the above-named reactants in the respective molar ratios of high molecular weight alkyl-substituted hydroxyaromatic compound, amine, and aldehyde of approximately 1.0:0.1–10:1–10. A suitable condensation procedure involves adding at a temperature of from about room temperature to 95° C., the aldehyde reagent (e.g., formalin) to a mixture of amine and alkyl-substituted hydroxyaromatic compounds alone or in an easily removed organic solvent, such as benzene, xylene, or toluene or in solvent-refined neutral oil, and then heating the reaction mixture at an elevated temperature (about 120° to 175° C.) while the water of reaction is distilled overhead and separated. The reaction product so obtained is typically finished by conventional filtration and dilution with solvent as desired.

Preferred Mannich reaction products used in the present invention are high molecular weight Mannich condensation products, formed by reacting an alkylphenol, an ethylene polyamine, and a formaldehyde-affording reactant in the respective molar ratios of 1.0:0.5–2.0:1.0–3.0, wherein the alkyl group of the alkylphenol has a number average weight of from about 300 to 5,000.

Representative of the high molecular weight alkyl-substituted hydroxyaromatic compounds are polypropylphenol, polybutylphenol, and other polyalkylphenols, with polyisobutylphenol being the most preferred. Polyalkylphenols may be obtained by the alkylation, in the presence of an alkylating catalyst such as $BF_3$, of phenol with high molecular weight polypropylene, polybutylene and other polyalkylene compounds to give alkyl substituents on the aromatic ring of phenol having a number average molecular weight of from about 300 to 5,000.

The alkyl substituents on the hydroxyaromatic compounds may be derived from high molecular weight polypropylenes, polybutenes, and other polymers of mono-olefins, principally 1-mono-olefins. Also useful are copolymers of mono-olefins with monomers copolymerizable therewith, wherein the copolymer molecule contains at least about 90% by weight of mono-olefin units. Specific examples are copolymers of butenes (1-butene, 2-butene, and isobutylene) with monomers copolymerizable therewith wherein the copolymer molecule contains at least about 90% by weight of propylene and butene units, respectively. Said monomers copolymerizable with propylene or said butenes include monomers containing a small proportion of unreactive polar groups, such as chloro, bromo, keto, ether, or aldehyde, which do not appreciably lower the oil-solubility of the polymer. The comonomers polymerized with propylene or said butenes may be aliphatic and can also contain non-aliphatic groups, e.g., styrene, methylstyrene, p-dimethylstyrene, divinyl benzene, and the like. From the foregoing limitation placed on the monomer copolymerized with propylene or said butenes, it is clear that said polymers and copolymers of propylene and said butenes are substantially aliphatic hydrocarbon polymers. Thus, the resulting alkylated phenols contain substantially alkyl hydrocarbon substituents having a number average molecular weight of from about 300 to 5,000.

In addition to the foregoing high molecular weight hydroxyaromatic compounds, other phenolic compounds which may be used include high molecular weight alkyl-substituted derivatives of resorcinol, hydroquinone, cresol, catechol, xylenol, hydroxy-di-phenyl, benzylphenol, phenethylphenol, naphthol, and tolylnaphthol, among others. Preferred for the preparation of such preferred Mannich condensation products are the polyalkylphenol reactants, e.g., polypropylphenol and polybutylphenol, particularly polyisobutylphenol, whose alkyl group has a number average molecular weight of about 300 to 5,000, preferably about 400 to 3,000, more preferably about 500 to 2,000, and most preferably about 700 to 1,500.

As noted above, the polyalkyl substituent on the polyalkyl hydroxyaromatic compounds employed may be generally derived from polyolefins which are polymers or copolymers of mono-olefins, particularly 1-mono-olefins, such as ethylene, propylene, butylene, and the like. Preferably, the mono-olefin employed will have about 2 to 24 carbon atoms, and more preferably, about 3 to 12 carbon atoms. More preferred mono-olefins include propylene, butylene, particularly isobutylene, 1-octene, and 1-decene. Polyolefins prepared from such mono-olefins include polypropylene, polybutene, especially polyisobutene, and the polyalphaolefins produced from 1-octene and 1-decene.

The preferred polyisobutenes used to prepare the presently employed polyalkyl hydroxyaromatic compounds are polyisobutenes which comprise at least about 20% of the more reactive methylvinylidene isomer, preferably at least about 50% and more preferably at least about 70% methylvinylidene isomer. Suitable polyisobutenes include those prepared using $BF_3$ catalysts. The preparation of such polyisobutenes in which the methylvinylidene isomer comprises a high percentage of the total composition is described in U.S. Pat. Nos. 4,152,499 and 4,605,808.

Examples of suitable polyisobutenes having a high alkylvinylidene content include Ultravis 10, a polyisobutene having a molecular weight of about 950 and a methylvinylidene content of about 76%, and Ultravis 30, a polyisobutene having a molecular weight of about 1,300 and a methylvinylidene content of about 74%, both available from British Petroleum, and Glissopal 1000, 1300 and 2200, available from BASF.

The preferred configuration of the alkyl-substituted hydroxyaromatic compound is that of a para-substituted mono-alkylphenol. However, any alkylphenol readily reactive in the Mannich condensation reaction may be employed. Accordingly, ortho mono-alkylphenols and dialkylphenols are also suitable for use.

Representative amine reactants are alkylene polyamines, principally polyethylene polyamines. Other representative organic compounds containing at least one >NH group suitable for use in the preparation of the Mannich reaction products are well known and include the mono- and di-amino alkanes and their substituted analogs, e.g., ethylamine, dimethylamine, dimethylaminopropylamine, and diethanolamine; aromatic diamines, e.g., phenylenediamine, diamino naphthalenes; heterocyclic amines, e.g., morpholine, pyrrole, pyrrolidine, imidazole, imidazolidine, and piperidine; melamine, and their substituted analogs.

The alkylene polyamine reactants which are useful include polyamines which are linear, branched, or cyclic; or a mixture of linear, branched, and/or cyclic polyamines wherein each alkylene group contains from about 1 to 10 carbon atoms. A preferred polyamine is a polyamine containing from about 2 to 10 nitrogen atoms per molecule or a mixture of polyamines containing an average of from about 2 to 10 nitrogen atoms per molecule such as ethylenediamine, diethylene triamine, triethylene tetramine, tetraethylene pentamine, pentaethylene hexamine, hexaethylene heptamine, heptaethylene octamine, octaethylene nonamine, nonaethylene decamine, and mixtures of such amines. Corresponding propylene polyamines such as propylene diamine, dipropylene triamine, tripropylene tetramine, tetrapropylene pentamine, and pentapropylene hexamine are also suitable reactants. A particularly preferred polyamine is a polyamine or mixture of polyamines having from about 3 to 7 nitrogen atoms, with diethylene triamine or a combination or mixture of ethylene polyamines whose physical and chemical properties approximate that of diethylene triamine being the most preferred. In selecting an appropriate polyamine, consideration should be given to the compatibility of the resulting Mannich detergent/dispersant with the gasoline fuel mixture with which it is mixed.

Ordinarily the most highly preferred polyamine, diethylenetriamine, will comprise a commercially available mixture having the general overall physical and/or chemical composition approximating that of diethylene triamine but which can contain minor amounts of branched-chain and cyclic species as well as some linear polyethylene polyamines such as triethylene tetramine and tetraethylene pentamine. For best results, such mixtures should contain at least about 50% and preferably at least about 70% by weight of the linear polyethylene polyamines enriched in diethylene triamine.

The alkylene polyamines are usually obtained by the reaction of ammonia and dihalo alkanes, such as dichloro alkanes. Thus, the alkylene polyamines are obtained from the reaction of about 2 to 11 moles of ammonia with about 1 to 10 moles of dichloro alkanes having about 2 to 6 carbon atoms and the chlorines on different carbons.

Representative aldehydes for use in the preparation of the high molecular weight Mannich reaction products include the aliphatic aldehydes such as formaldehyde, acetaldehyde, propionaldehyde, butyraldehyde, valeraldehyde, caproaldehyde, heptaldehyde, and stearaldehyde. Aromatic aldehydes that may be used include benzaldehyde and salicylaldehyde. Illustrative heterocyclic aldehydes for use herein are furfural and thiophene aldehyde, etc. Also useful are formaldehyde-producing reagents such as paraformaldehyde, or aqueous formaldehyde solutions such as formalin. Most preferred is formaldehyde, formalin, or paraformaldehyde.

The Filtration Method

As discussed previously, the present invention relates to the removal of excess water-soluble amines in the preparation of Mannich condensation products. In a typical procedure for carrying out the present invention, the diluted crude Mannich condensation product is charged to a well-agitated vessel such as a filter-feed tank. With stirring, the vessel is heated to a temperature range of about 40° to 95° C. The preferred temperature range is about 50° to 85° C. and more preferably about 60° to 75° C. The vessel may be kept under a nitrogen pressure of about 0 to 20 psig to minimize water vapor generation. The preferred pressure range is about atmospheric to 5 psig, and the more preferred pressure is atmospheric pressure.

After the desired temperature has been reached, magnesium silicate, such as Magnesol, a synthetic magnesium silicate manufactured by The Dallas Group of America, is thoroughly mixed with the diluted crude Mannich condensation product in the filter-feed vessel.

Typically, about 90 to 230 g of magnesium silicate will be employed per equivalent of water-soluble amine in the diluted crude Mannich product, preferably about 100 to 200 g per equivalent, and more preferably about 110 to 180 g of magnesium silicate per equivalent of water-soluble amine.

When employed, a filter aid in the amount of about 0.1 to 2%, based on the diluted crude Mannich condensation product, is added and thoroughly mixed. The primary purpose of the filter aid is to improve the filtration of the magnesium silicate, although it also has some limited water-soluble amine removal capability. The amount of the filter aid required will depend on the filtration characteristics of the grade of magnesium silicate used. The preferred range of filter aid is about 0.2 to 1.5%, and the most preferred range is about 0.3 to 1%. Typically, the filter aid will be employed when the particle size distribution of the magnesium silicate is such that the average particle size is below about 50 microns. However, the filter aid may also optionally be employed in amounts of about 0.1 to 2%, based on the diluted crude Mannich condensation product, when the particle size distribution of the magnesium silicate is such that the average particle size is equal to or greater than about 50 microns.

In general, the amount of filter aid is optimized for the grade of magnesium silicate used so as to yield an economical filtration rate and minimize product loss in the filter cake. Although the filter aid provides some small benefit for amine removal, it is mainly employed to assure a high enough filtration rate.

Suitable filter aids for use in the present invention include diatomaceous earth (diatomite, kieselguhr, infusorial earth), perlite, asbestos fibers, such as chrysotile, cellulose fibers, such as Solka Floc, carbon-based filter aids, fly ash, and plastics, such as Gellfilt, made from foamed polyurethane. Mixtures of filter aids may also be employed. A preferred filter aid is diatomaceous earth.

The charge order of the magnesium silicate and the filter aid, when employed, is not particularly significant. However, the degree of mixing is an important consideration. The magnesium silicate and filter aid should be mixed to uniformity in the diluted crude Mannich condensation product with no settling in the bottom of the tank.

The diluted crude Mannich condensation product, magnesium silicate, and filter aid are thoroughly mixed for about 0.25 to 2 hours, preferably for about 0.4 to 1.5 hours, and most preferably about 0.5 to 1 hour, at the temperature ranges described above, that is, about 40° to 95° C., preferably about 50° to 85° C., and more preferably about 60° to 75° C.

At this point, water is added to the above mixture. Deionized or distilled water is preferred so as not to introduce excess minerals into the product.

Typically, about 20 to 150 g of water will be employed per equivalent of water-soluble amine to be removed, preferably about 35 to 85 g, and more preferably about 45 to 70 g of water per equivalent of water-soluble amine.

Here, the order of addition is typically an important consideration, particularly when a filter aid is present. The water should be added after the magnesium silicate and filter aid are thoroughly mixed with the diluted crude Mannich condensation product. This will ensure that the wetting of the magnesium silicate and filter aid is uniform, the solids remain mixed in the diluted crude Mannich with no solids settling in the bottom of the vessel, and water loss from evaporation is minimal.

The crude Mannich condensation product, magnesium silicate, filter aid and water are thoroughly mixed for about 0.25 to 3 hours, preferably for about 0.4 to 2 hours, and most preferably about 0.5 to 1 hour, at the temperature ranges described above, that is, about 40° to 95° C., preferably about 50° to 85° C., and more preferably about 60° to 75° C. The temperature must be kept below 100° C. to avoid the generation of more water-soluble amine, including amine-formaldehyde intermediates, through chemical equilibrium as these water-soluble amines are being removed.

When utilized, a precoat layer of filter aid is placed onto a pressure filter screen or media to give a thickness of about 2 to 3 mm. However, even when a filter aid is not used with the magnesium silicate, the filter screen may still be precoated with filter aid to facilitate filtration. The diluted crude product is fed to the filter and filtered under pressure up to about 100 psig. Typical final filtration pressures are in the range of about 30 to 60 psig. The filtration is typically carried out at the same temperature as the above mixing of the Mannich condensation product, magnesium silicate, filter aid, and water. The choice of filter aid type as well as the exact water charge can be determined to give a water-soluble amine concentration in the product below about 0.05 mEq/g and an acceptable filtration rate for a manufacturing plant. The filtrate containing the Mannich condensation product having less than about 0.05 mEq/g of water-soluble amine is recovered and then analyzed for water-soluble amine concentration.

When the magnesium silicate particle size distribution is such that the average particle size is greater than about 50 microns, the use of filter aid is not necessary. The crude mixture of diluted Mannich product, magnesium silicate, and water is circulated through the filter and back to the feed tank until a precoat layer of solids is formed on the filter screen. Once there is a precoat layer and the filtrate is clear, the recirculation of filtrate to the feed tank is stopped and the filtered Mannich product having less than about 0.05 mEq/g of water-soluble amine is routed to a finished product tank.

EXAMPLES

The invention will be further illustrated by the following examples, which set forth particularly advantageous method embodiments. While the Examples are provided to illustrate the present invention, they are not intended to limit it.

Example 1

Mannich Condensation Product

A Mannich condensation product was produced in a reactor equipped with a distillation column and an overhead Dean-Stark trap system by the following general procedure. A solution of polyisobutylphenol in Solvesso Aromatic 100 solvent was charged to the reactor at about 40° to 45° C. Solvesso Aromatic 100 solvent is manufactured by Exxon-Mobil Chemical Company. The polyisobutylphenol was produced from polyisobutylene containing at least 70% methylvinylidene isomer as described in U.S. Pat. No. 5,300,701. The polyisobutylphenol had a nonvolatile residue of 62.1% and a hydroxyl number of 39.1 mg KOH/g. Diethylenetriamine (DETA) having an assay of 99.2% was charged to the reactor in the ratio one mole of DETA per mole of polyisobutylphenol and thoroughly mixed with the polyisobutylphenol. Heating of the reactor was started after charging of the DETA. When the reactor temperature was about 55° to 60° C., paraformaldehyde, having a purity of 91.9%, was charged to the reactor. The charge ratio was two moles of formaldehyde per mole of polyisobutylphenol. The temperature was increased over three hours to about 175° to 177° C. and the pressure gradually lowered to about 520 to 540 mm Hg. As byproduct water formed, water and solvent vapor distilled from the reactor and passed up through the distillation column. The byproduct water and solvent were separated and the solvent returned to the column as reflux so that no net solvent was taken overhead. The final temperature and pressure were held for 6 hours to make sure the Mannich condensation reaction went to completion. The Mannich condensation product was cooled to 40° C., transferred to a filter-feed tank, and polished filtered using a filter precoat of HyFlo Super Cel filter aid. Crude product was used as the precoat liquor, and then the Mannich condensation product was passed through the filter without any filter aid as body feed. HyFlo Super Cel filter aid is a diatomaceous earth manufactured by World Minerals Incorporated.

The Mannich condensation product was clear (0% haze using Nippon Denshoku Model 300A haze meter), light gold in color (2.5 by ASTM D1500), and contained 2.8% nitrogen and 70% nonvolatile residue. A 3-gram sample of the Mannich condensation product was diluted with 100 mL of hexane and 0.1 mL of demulsifier and then extracted twice with 40 mL of warm water. The water extract was titrated with 0.1 N hydrochloric acid. The water-soluble amine content was measured as 0.176 mEq/g.

In another analytical method, 2 g of the Mannich condensation product was diluted with 0.5 g of n-butanol and 1 g of deionized water in a vial and thoroughly mixed. After phase separation, the aqueous layer was recovered and analyzed by gas chromatography (GC). Reference standards and mass spectroscopy were used to identify the major peaks. Based on this analysis, the Mannich condensation product contained 0.61% DETA and 0.16% of 1-(2-aminoethyl), 3-isodiazolidine (DETA with one formaldehyde-derived methylene group bridging two adjacent nitrogens). There were other DETA-formaldehyde compounds present, but the major constituent was 1-(2-aminoethyl), 3-isodiazolidine. The GC method does not account for all of the water-soluble amine measured by the titration method because not all GC peaks are quantified and because of differences in the extraction procedures.

This Mannich condensation product is used in the further examples to demonstrate the effectiveness of magnesium silicate in reducing the concentration of water-soluble amine to less than 0.05 mEq/g.

Example 2

Mannich Condensation Product

Following the same procedure and charge mole ratios as in Example 1, a second batch of Mannich condensation product was produced. The starting polyisobutylphenol had a nonvolatile residue of 67.5% and a hydroxyl number of 40.0 mg KOH/g. The DETA had an assay of 99.2% and the paraformaldehyde an assay of 91.6%. The Mannich condensation product was cooled to 60° C. and transferred to storage without the need for filtering.

The Mannich condensation product was clear (1% haze using Nippon Denshoku Model 300A haze meter), light gold in color (2.5 by ASTM D1500), and contained 2.7% nitrogen and 72% nonvolatile residue. The water-soluble amine content was measured as 0.176 mEq/g, giving the same result as in Example 1.

The gas chromatography analysis indicated that the Mannich condensation product contained 0.65% DETA and 0.15% of 1-(2-aminoethyl), 3-isodiazolidine. Again, there were other DETA-formaldehyde compounds present, but the major constituent was 1-(2-aminoethyl), 3-isodiazolidine.

Like Example 1, the Example 2 batch of diluted crude Mannich condensation product is used in the further examples to demonstrate the effectiveness of magnesium silicate in reducing the water-soluble amine concentration to less than about 0.05 mEq/g.

Example 3

Mannich Condensation Product

A Mannich condensation product was produced using the typical procedures described in Examples 1 and 2 except as follows. The polyisobutylphenol had a nonvolatile residue of 73.9% and a hydroxyl number of 41.4 mg KOH/g. The diethylenetriamine (DETA) had an assay of 98.3% and the paraformaldehyde, had a purity of 92.5%. Three moles of formaldehyde per mole of polyisobutylphenol were used. The Mannich condensation product was cooled to about 45° to 50° C., diluted to 69.8% nonvolatile residue with Exxon Aromatic 100 solvent, and filtered.

The filtered Mannich condensation product was clear (3.4% haze using Nippon Denshoku Model 300A haze meter), light gold in color (2.5 by ASTM D1500), and contained 2.5% nitrogen. The water-soluble amine content was measured as 0.074 mEq/g.

This Mannich condensation product is used in Examples 10 and 11 to establish an acceptable maximum limit for water-soluble amine in formulation compatibility and air sensitivity tests.

Example 4

Magnesium Silicate without Filter Aid

In this example a grade of magnesium silicate was used that has a relatively coarse particle size distribution so that filter aid was not needed in order to achieve a typically acceptable filtration rate. Table 1 compares the particle size ranges of some typical magnesium silicate samples measured in a dilute slurry using water with a Malvern Master-Sizer MS20 light-scattering instrument.

TABLE 1

Typical Particle Sizes for Various Magnesium Silicates

| Sample | Vol. Mean Diameter in microns | % of Particles Smaller than 30 microns |
| --- | --- | --- |
| Celkate T-21 | 15.8 | 83 |
| Magnesol HMR-LS | 35.2 | 46 |
| Magnesol Polysorb | 48.4 | 34 |
| Magnesol Cartridge | 60.1 | 16 |

Celkate T-21 is magnesium silicate manufactured by World Minerals Inc. Magnesol is magnesium silicate produced by The Dallas Group of America, Inc. Cartridge Grade Magnesol has an average particle diameter of about 60 microns (volumetric mean diameter) and only 16% of the particles are smaller than 30 microns in diameter. In contrast, Celkate T-21 has an average particle diameter of 15.8 microns and 83% of the particles have diameters smaller than 30 microns. Therefore, Celkate T-21 contains a much greater number of small diameter particles than Cartridge Grade Magnesol making it much more difficult to filter (low filtration rates) from the diluted crude Mannich condensation product. All of these magnesium silicates except for Cartridge Grade Magnesol require varying amounts of filter aid in order to obtain an economically acceptable filtration rate. The Cartridge grade of magnesium silicate does not require the use of filter aid and typically yields filtration rates in excess of 200 kg/h/m$^2$.

3,000 g of diluted crude Mannich condensation product (Example 2), containing about 72% Mannich product in Solvesso Aromatic 100 solvent, were charged to a 4-L filter-feed tank equipped with agitation and heating a heating system. The diluted crude Mannich was heated to about 60° to 65° C. To this was added 75 g of Cartridge Grade Magnesol (142 g magnesium silicate/equivalent of water-soluble amine). The magnesium silicate was mixed vigorously with the Mannich condensation product for 6 minutes to make sure the solids were evenly dispersed. 30 g of water (56.8 g water/equivalent of water-soluble amine) and 89.8 g of unfiltered crude Mannich product recovered from the previous filtration were added and mixed with the Mannich condensation product and magnesium silicate for 33 minutes. The crude mixture was then pumped through a pressure filter having an area of 0.00994 m$^2$ and the filtrate sent back to the filter-feed tank until it appeared clear. The filter was maintained at the same temperature as the feed tank. There was no filter aid used and the filter screen was not given a precoat layer of filter aid. After circulating for 22 minutes, the filtrate was diverted to a 1-gallon jar on a weigh scale. 2,881 g of filtrate were collected. The average filtration rate was 448 kg/h/m$^2$ at a maximum pressure of 60 psig.

Analysis of the filtrate showed that it contained 0.026 mEq/g of water-soluble amine. The sample contained 0.042% DETA and 0.020% 1-(2-aminoethyl), 3-isodiazolidine by the GC analysis described in Example 1. The filtrate was clear (0.6% haze using Nippon Denshoku Model 300A haze meter) and had a color of 3.0 using ASTM D1500 color scale. The color of the sample of Example 2 was 2.5 before magnesium silicate filtration.

Example 5

Magnesium Silicate with Filter Aid

Using the pressure filter system described in Example 4, 1,491 g of Hi-Sol 10 aromatic solvent and 14 g of HyFlo Super Cel filter aid were circulated through the filter from the filter-feed tank to give a precoat layer of about 3 mm on the filter screen. The precoat solvent was then drained from the filter system and 1,463 g was recovered.

2,500 g of diluted crude Mannich condensation product (Example 1), containing about 70% Mannich product in Solvesso Aromatic 100 solvent, were charged to the filter-feed tank and heated to about 60° to 65° C. To this was added 75 g of HMR-LS Grade of Magnesol (170 g magnesium silicate/equivalent of water-soluble amine) as described in Example 4 and Table 1. The typical average particle size of the HMR-LS Grade of Magnesol is well below 50 microns as shown in Table 1, and is nearly half the average particle size of the Cartridge Grade Magnesol. Therefore, it is necessary to use filter aid with HMR-LS Grade of Magnesol in order to achieve a viable filtration rate.

The magnesium silicate was mixed vigorously with the diluted crude Mannich condensation product for 5 minutes to make sure the solids were evenly dispersed. 12.5 g of HyFlo Super Cel filter aid was added next and mixed for 5 minutes with the diluted crude Mannich condensation product and the magnesium silicate. 25 g of deionized water (56.8 g water/equivalent of water-soluble amine) were charged and mixed with the diluted crude Mannich condensation product, magnesium silicate, and filter aid for 30 minutes at about 60° to 65° C. The crude mixture was then pumped through the pressure filter and the filtrate sent back to the filter-feed tank until it appeared clear. After circulating for 15 minutes, 2,188 g of filtrate was collected in a 1-gallon jar on a weigh scale. The filter was maintained at the same temperature as the feed tank. The average filtration rate was 211 kg/h/m² at a maximum pressure of 60 psig.

Analysis of the filtrate showed that it contained 0.033 mEq/g of water-soluble amine. The filtrate was clear (0.3% haze using Nippon Denshoku Model 300A haze meter) and a color of 4.0 using ASTM D1500 color scale. The color of the diluted crude Mannich condensation product in Example 2 was 3.0 before the magnesium silicate filtration. The filtrate contained 68.3% nonvolatile residue.

Example 6

Comparative Examples Using Filter Aid without Magnesium Silicate

Diatomaceous earth is a siliceous material composed of the skeletal remains of microscopic aquatic plants called diatoms. It is composed of aluminosilicate and various elements such as iron, calcium, sodium, and magnesium. As such, it has a limited amount of surface activity for absorption of water-soluble amines but is less active than synthetic magnesium silicate. Three comparative conventional filtrations in this example illustrate how large amounts of filter aid are needed to even approach the effectiveness of magnesium silicate. This is not considered to be an economically viable approach because of the relatively high costs associated with product loss and waste disposal.

The procedure for the three experiments was as follows. 500 g of diluted crude Mannich condensation product (Example 2) containing about 72% Mannich product in Solvesso Aromatic 100 solvent were charged to a 1-L Morton type reaction flask equipped with an agitator and heating mantel with temperature control. After heating the Mannich product to 60° C., 20 g of HyFlo Super Cel filter aid (4% based on diluted crude Mannich condensation product) were added and mixed with the diluted crude Mannich condensation product for 5 minutes. Next, water was added in the amount specified in Table 2 for each experiment and mixed with the other ingredients for 30 minutes at 60° C. Whatman No. 2 filter paper was put on the screen of a batch, cylindrical pressure filter having an area 1.113×10⁻² m². A filter aid precoat layer of about 2 to 3 mm thickness was prepared by placing 16 g of HyFlo Super Cel on top of the filter paper in a dry form. It was spread evenly using the bottom of a beaker. The temperature control on the jacket of the filter was set to maintain about 60° to 65° C.

The crude was charged to the pressure filter and filtered at about 60° to 65° C. and a maximum pressure of about 60 to 90 psig. Filtrate rates were in the range about 543 to 558 kg/h/m².

TABLE 2

Effect of Filter Aid on Removing Water-Soluble Amine

| Comparative Example (test #) | Water, g/Eq of water-soluble amine | Filtrate Water-soluble Amine, mEq/g | Haze, % |
|---|---|---|---|
| 6-1 (J3) | 56.8 (1%) | 0.054 | 85.4 |
| 6-2 (J3R) | 56.8 (1%) | 0.042 | 38.5 |
| 6-3 (J4) | 28.4 (0.5%) | 0.075 | 68.2 |

The comparative results in Table 2 show that with an excessive amount of filter aid, it is possible to reduce the water-soluble amine concentration below about 0.05 mEq/g in the Mannich condensation product. However, the data in Table 2 suggest that it is not possible to achieve a water-soluble concentration below about 0.04 mEq/g without using an even larger excess of filter aid. The filter aid does remove much of the amine, but is not as effective as a lesser amount of the magnesium silicate as shown in Examples 4 and 5. Therefore, product loss and waste disposal costs will be relatively high if large amounts of filter aid are used.

Another key point is that the filter aid is not as effective in absorbing the water used in the treatment. If the Mannich product remains hazy from water after the treatment, a drying step may be necessary to eliminate dispersed water and reduce the haze. Under optimum conditions, magnesium silicate eliminates the need for a drying step. Thus, the use of filter aid alone is not considered an economically viable option.

Example 7

Effect of Water Quantity

Water is an essential ingredient is removing the water-soluble amine. The amine is very soluble in water and water is rapidly absorbed by the active surface of the magnesium silicate. In a series of four experiments, we varied the amount of water charged while keeping the amount of magnesium silicate and filter aid constant. The procedure for each of the four experiments was similar to that described in Example 6 except as follows. 500 g diluted crude Mannich condensation product (Example 2) containing about 72% Mannich product in Solvesso Aromatic 100 solvent was charged to a 1-L Morton type reaction flask equipped with an agitator and heating mantel with temperature control. After heating the Mannich product to 60° C., 15 g of magnesium silicate (HMR-LS Grade from The Dallas Group of America, Inc.) was added and mixed with the Mannich for 5 minutes. Next, 5 g of HyFlo Super Cel was added and mixed with the Mannich and magnesium silicate for 5 minutes. Lastly, the water was added (0%, 0.2%, or 1%, depending on the experiment) and mixed with the other ingredients for 30 minutes. A precoat layer of about 2 to 3 mm thickness was put on the screen of a batch, cylindrical pressure filter having an area 1.113×10⁻² m² as described in Example 6. The crude was charged to the pressure filter and filtered at about 60° to 65° C. and a maximum pressure of about 60 to 90 psig. Filtrate rates were in the range about 212 to 373 kg/h/m².

The results of these tests are given in Table 3.

TABLE 3

Effect of Water Concentration

| Example (test #) | Water, g/Eq of water-soluble amine | Filtrate Water-soluble Amine, mEq/g | Haze, % |
|---|---|---|---|
| 7-1 (J1) Comparative | 0.0 (0%) | 0.101 | 37.6 |
| 7-2 (J8) Comparative | 11.4 (0.2%) | 0.076 | 4.1 |
| 7-3 (J2) | 56.8 (1%) | 0.029 | 0.2 |
| 7-4 (J5) | 56.8 (1%) | 0.030 | 0.0 |

Thus, the data in Table 3 show that it is critical that an adequate amount of water is used in order to reduce the water-soluble amine concentration to less than 0.05 mEq/g.

Example 8

Effect of Magnesium Silicate Quantity

The pressure filter described in Examples 4 and 5 was precoated using Exxon Aromatic 100 solvent and 14 g of HyFlo Super Cel filter aid following the procedure given in Example 5.

About 2,500 to 3,000 g of diluted crude Mannich condensation product (Example 1) containing about 70% Mannich product in Solvesso Aromatic 100 solvent were charged to the filter-feed tank and heated to about 60° to 65° C. To this was added different amounts of HMR-LS Grade Magnesol (magnesium silicate supplied by The Dallas Group of America, Inc.) and HyFlo Super Cel according to Table 4. The magnesium silicate and filter aid were mixed vigorously with the diluted crude Mannich condensation product for 5 minutes to make sure the solids were evenly dispersed. About 55 to 57 g of deionized water per equivalent of water-soluble amine were charged and mixed with the diluted crude Mannich condensation product, magnesium silicate, and filter aid for 30 minutes at about 60° to 65° C. The crude mixture was then pumped through the pressure filter and the filtrate sent back to the filter-feed tank until it appeared clear. After circulating for 15 minutes, filtrate was collected in a 1-gallon jar on a weigh scale. The filter was maintained at the same temperature as the feed tank, except in Example 8-1 where the filter temperature was 78° C. The average filtration rates for these experiments were in the range about 290 to 526 kg/h/m$^2$ at a maximum pressure of 60 psig (except Example 8-1 where the final pressure was 26 psig and Example 8-5 where the final pressure was at 81 psig).

The results in Table 4 show that the amount of water-soluble amine and the haze due to the water used in the treatment both decreased as the charge of magnesium silicate is increased. The percent haze undergoes essentially a step change increase when the quantity of magnesium silicate and filter aid are not sufficient to remove most of the water. This can often dictate how much magnesium silicate should be used. However, if a low-temperature drying step is added after the treatment, the haze is not critical. Since the filter aid has some absorption capacity for water-soluble amine, the combination of the magnesium silicate and filter aid must be optimized for each particular raw material combination as illustrated by Examples 8-2 and 8-3.

TABLE 4

Effect of Magnesium Silicate Quantity

| Example | Magnesol HMR-LS, g/Eq water-soluble amine | Filter Aid, % | Filtrate Water-soluble Amine, mEq/g | Haze, % |
|---|---|---|---|---|
| 8-1 (J30) Comparative | 85.2 (1.5%) | 0.3 | 0.056 | 69.1 |
| 8-2 (J54) | 114 (2%) | 0.5 | 0.042 | 67.6 |
| 8-3 (J41) | 114 (2%) | 1.0 | 0.037 | 6.8 |
| 8-4 (J52) | 142 (2.5%) | 1.0 | 0.034 | 4.1 |
| 8-5 (J31) | 170 (3%) | 1.0 | 0.031 | 1.3 |

Example 9

Preparation of Additional Treated Mannich Product Samples for Formulation Tests

Four additional samples of varying water-soluble amine content were produced using the filtration methods similar to those described in the previous examples.

Examples 9-1, 9-3, and 9-4 were prepared by the following procedure with the exception that Example 9-1 used diluted crude Mannich condensation product from Example 1 and the rest used diluted crude Mannich condensation product from Example 2. About 3,000 to 3,700 g of diluted crude Mannich condensation product (Examples 1 or 2) containing about 70 to 72% Mannich product in Solvesso Aromatic 100 solvent were charged to a 5-L tank equipped with an agitator and heating jacket with temperature control. After heating the Mannich product to 60° C., about 56.8 to 170 g of magnesium silicate (HMR-LS Grade from The Dallas Group of America, Inc.) per equivalent of water-soluble amine was added and mixed with the Mannich for 5 minutes. Table 5 shows the relative charges for each sample. Next, about 0.2 to 1% HyFlo Super Cel on diluted crude Mannich condensation product was added and mixed with the Mannich and magnesium silicate for 5 minutes. Lastly, about 45.7 to 57.0 g of water per equivalent of water-soluble amine were added and mixed with the other ingredients for 30 minutes. A precoat layer of about 2 to 3 mm thickness was put on the screen of a batch, cylindrical pressure filter having an area 1.113×10$^{-2}$ m$^2$ as described in Example 6. The crude was charged to the pressure filter and filtered at about 60° to 65° C. and a maximum pressure of about 60 to 90 psig. Filtrate rates were in the range about 115 to 345 kg/h/m$^2$. The results of these tests are given in Table 5.

Example 9-2 was prepared following the same procedure described in Example 8 except with the relative charges listed in Table 5. Filtrate rates were in the range about 376 to 424 kg/h/m$^2$. The results of these tests are given in Table 5.

TABLE 5

Preparation of Additional Mannich Product Samples

| Example (test #) | Magnesol HMR-LS, g/Eq water-soluble amine | Water, g/Eq water-soluble amine | Filter Aid, % on diluted crude Mannich product | Filtrate Water-soluble Amine, mEq/g | Haze, % |
|---|---|---|---|---|---|
| 9-1 (J25) Comparative | 56.8 (1%) | 45.7 (0.8%) | 0.2 | 0.070* | 93.1 |
| 9-2 (J43) | 114 (2%) | 45.4 (0.8%) | 0.5 | 0.042 | 30.5 |
| 9-3 (J39) | 114 (2%) | 56.8 (1%) | 1.0 | 0.039 | 8.1 |
| 9-4 (J32) | 170 (3%) | 57.0 (1%) | 1.0 | 0.034 | 0.5 |

*A portion of Example 9-1 was subsequently dried for 30 minutes at 12 mm Hg and 64° C. using a 250-mL Morton flask and Dean-Stark trap. The dried sample contained 0.058 mEq/g water-soluble amine and 0.3% haze.

Comparative Example 9-1 has a water-soluble amine concentration above the target maximum of 0.05 mEq/g because not enough magnesium silicate was used.

Example 10

Comparative Compatibility and Air Sensitivity of Formulation with Untreated Mannich Condensation Product A typical formulation was blended at room temperature with treated Mannich condensation product and was used to test the effect of water-soluble amine concentration in the Mannich product on the compatibility and air sensitivity of the formulation with other components. The formulation is shown in Table 6. Light alkylate solvent is an aromatic solvent manufactured by Chevron Oronite S.A.

TABLE 6

Typical Compatibility and Air Sensitivity Test Formulation

| Component | Weight Percent |
|---|---|
| Mannich condensation product | 30 |
| Light alkylate solvent | 38.8 |
| Synthetic carrier fluid | 30 |
| Demulsifier | 0.4 |
| Corrosion inhibitor | 0.8 |

Mannich condensation product formulation compatibility is measured at room temperature in a 100-mL cylindrical oil sample bottle made of clear glass and filled with the formulation. A cork is inserted into the mouth of the bottle to keep out air. The sample is stored in a rack open to the light in the room. Two qualitative visual rating scales are used; one for fluid appearance with ratings in the range of 0 to 6, and one for the amount of sedimentation with ratings in the range 0 to 4. A low rating number indicates good compatibility and a high rating number indicates poor compatibility. For example, an appearance rating of 6 means the formulation contained heavy cloud (close to opaque). A rating of 4 for sedimentation indicates the presence of a large amount of sediment in the bottom of the bottle. The typical requirement for a pass in this test is a fluid appearance rating in the range of 0 to 2 (absolutely bright to slight cloud) and a sedimentation rating of 0 to 1 (no sediment to very slight sediment).

The air sensitivity of the test formulation containing treated Mannich condensation product is measured at room temperature using about 100 g of sample in a 250-mL beaker that is open to the air. A 500-mL beaker is inverted over the 250-mL beaker to keep out air drafts that would quickly cause solvent evaporation, while still allowing equilibration with the surrounding air. The beaker is weighed at the end to make sure the weight loss due to solvent evaporation is less than about 5%. If enough solvent is lost, phase separation can occur. The air sensitivity test uses the same rating scales as the compatibility test. Both tests are supplemented when possible with haze measurements using a Nippon Denshoku Model 300A haze meter.

Diluted crude Mannich condensation product from Examples 1 and 2, each containing 0.176 mEq/g of water-soluble amine, were evaluated in the compatibility test for up to 30 days. Similarly, the diluted crude Mannich condensation product from Example 3, containing 0.074 mEq/g of water-soluble amine, was evaluated in the compatibility test for 30 days. All three diluted crude Mannich condensation product samples caused failures in the formulation compatibility test.

The formulation that contained diluted crude Mannich condensation product from Example 1 failed immediately after blending due to cloud formation and had a haze of 55.1% after 30 days.

The formulation that contained diluted crude Mannich condensation product from Example 2 failed the test immediately after blending due to haze, floc, and sediment. The percent haze after 30 days for three different samples was in the range about 36.6 to 58.8%. Percent haze over about 15 to 20% is considered unacceptable.

The formulation that contained diluted crude Mannich condensation product from Example 3 failed after one day in the closed bottle with a 3/0 rating. The final haze at 30 days was 43.8%.

Since all three samples did poorly in the compatibility test, no air sensitivity tests were conducted.

TABLE 7

Comparative Formulation Compatibility with Untreated Mannich Condensation Product

| Example | Blend | Fluid/Sediment Rating in Compatibility Test Initial | 7-days | 30-days | % Haze (30-days) |
|---|---|---|---|---|---|
| 1 | 10 | 3/0 | 3/0 | 6/2 | 55.1 |
| 2 | 9 | 3/0 | 6/0 | 6/2 | 58.8 |
| 2 | 11 | 4/2 | 3/2 | 3/3 | 36.6 |

TABLE 7-continued

Comparative Formulation Compatibility with Untreated Mannich Condensation Product

| | | Fluid/Sediment Rating in Compatibility Test | | | % Haze |
|---|---|---|---|---|---|
| Example | Blend | Initial | 7-days | 30-days | (30-days) |
| 2 | 13 | 4/1 | 3/2 | 3/0 | 41.8 |
| 3 | 33 | 2/0 | 3/0 | 3/0 | 43.8 |

Example 11

Improved Formulation Compatibility and Air Sensitivity with Treated Mannich Condensation Product A threshold value of 0.05 mEq/g was established as a maximum target for water-soluble amine concentration. This represents what is typically acceptable for an additive customer's storage tank.

Table 8 lists the formulation compatibility of Mannich condensation product samples that contained water-soluble amine in the concentration range of about 0.029 to 0.101 mEq/g. Blends 100 to 107 used Mannich condensation product that had undergone treatment with magnesium silicate as described in the Examples 7 to 9.

Blend numbers 78 and 79 were made using comparative Example 7-1 (0.101 mEq/g water-soluble amine concentration) and inventive Example 7-3 (0.029 mEq/g water-soluble amine concentration). Blend number 33 from Table 7 is repeated in Table 8 to add clarity to the comparative data. Sample 7-3 contained 0.037% DETA and 0.016% 1-(2-aminoethyl), 3-isodiazolidine according to GC analysis by the procedure described in Example 1.

The formulation using comparative Example 7-1 failed the compatibility test within 10 days and was hazy (25.4%) at the start. At the end of the 30-day test, the haze was 40.8%. Similarly, the formulation made with comparative Example 3 (Blend 33) condensed Mannich product failed the compatibility test by the end of 30 days. The formulation made with invention Example 7-3 had a rating of 0/0 and had a haze measurement of 0.2% after 30 days. This brackets the acceptable threshold for water-soluble amine concentration between about 0.03 and 0.07 mEq/g. Examples 7-1 and 3 are clearly out side the scope of this invention, and air sensitivity test data will show that Examples 8-1 and 9-1 are also outside the scope of this invention.

TABLE 8

Formulation Compatibility Using a Range of Treated Mannich Samples

| Blend (Example) | Mannich water-soluble amine | Fluid/Sediment Rating in Compatibility Test | | End Rating | % Haze (end) |
|---|---|---|---|---|---|
| | | Initial | End-days | | |
| 78 (7-1) Comparative | 0.101 | 2/0 (25.4%) | 10 days | 3/0 | 40.8 |
| 33 (3) Comparative | 0.074 | 2/0 | 30 days | 3/0 | 43.8 |
| 101 (9-1) Comparative | 0.058 | 0/0 (0%) | 30 days | 0/0 | 0.0 |
| 106 (8-1) Comparative | 0.056 | 0/0 (0.5%) | 30 days | 0/0 | 0.1 |
| 107 (9-2) | 0.042 | 0/0 (0.2%) | 30 days | 0/0 | 0.0 |
| 103 (9-3) | 0.039 | 0/0 (0%) | 30 days | 0/0 | 0.1 |
| 100 (9-4) | 0.034 | 0/0 (0%) | 30 days | 0/0 | 0.0 |
| 79 (7-3) | 0.029 | 0/0 (0%) | 30 days | 0/0 | 0.2 |

Next, the five samples in Table 9 were evaluated in formulation air sensitivity tests using treated Mannich product derived from the diluted crude Mannich condensation product in Example 1. The samples contained water-soluble amine in the concentration range of about 0.034 to 0.058 mEq/g. All of them had undergone treatment with magnesium silicate as described in the Examples 7-9. All of these samples passed the compatibility test after 30 days with ratings of 0/0 and contained essentially no measurable haze as shown previously in Table 8.

TABLE 9

Air Sensitivity Test of a Range of Treated Mannich Samples

| Blend (Example) | Mannich water-soluble amine | Fluid/Sediment Rating in Air Sensitivity Test | | | % Haze (end) |
|---|---|---|---|---|---|
| | | Initial (haze %) | 7 to 8-days | 30-days | |
| 101 (9-1) Comparative | 0.058 | 0/0 (0.0%) | 2/2 | 0/2 | 0.1 |
| 106 (8-1) Comparative | 0.056 | 0/0 (0.5%) | 0/0 | 6/0 | 58.2 |
| 107 (9-2) | 0.042 | 0/0 (0.2%) | 0/1 | 0/0 | 0.2 |
| 103 (9-3) | 0.039 | 0/0 (0.0%) | 0/1 | 0/0 | 0.1 |
| 100 (9-4) | 0.034 | 0/0 (0.0%) | 0/0 | 0/0 | 0.0 |

The two samples that contained 0.056 and 0.058 mEq/g of water-soluble amine (blend numbers 101 and 106) gave failing results in the air sensitivity test. Blend 101 failed after three days due to cloud formation with a rating of 3/1. The cloud gradually settled and gave an unacceptable amount of sediment and a failing rating of 2/2 at 8 days, and 0/2 after 30 days. Blend 106 failed after 14 days due to heavy cloud, ending with a 6/0 rating at 30 days. Blend 106 had a final haze of 58.2%. Based on the above air sensitivity measurements, an acceptable maximum value for water-soluble amine concentration of 0.05 mEq/g was established.

While the present invention has been described with reference to specific embodiments, this application is intended to cover those various changes and substitutions that may be made by those skilled in the art without departing from the spirit and scope of the appended claims.

What is claimed is:

1. A method of removing excess water-soluble amines from a diluted crude Mannich condensation product containing about 40 to 80 weight percent crude Mannich condensation product in an inert solvent, said method comprising:

a) filtering the diluted crude Mannich condensation product in the presence of about 90 to 230 g of magnesium silicate per equivalent of water-soluble amine in the diluted crude Mannich condensation product and about 20 to 150 g of water per equivalent of water-soluble amine in the diluted crude Mannich condensation product, and in the further presence of about 0.1 to 2%, based on the diluted crude Mannich condensation product, of a filter aid when the particle size distribution of the magnesium silicate is such that the average particle size is below about 50 microns; and b) recovering a filtrate containing a Mannich condensation product having less than about 0.05 mEq/g of water-soluble amine.

2. The method according to claim 1, wherein the Mannich condensation product is a product of (1) a high molecular weight alkyl-substituted hydroxyaromatic compound wherein the alkyl group has a number average molecular weight of from about 300 to 5,000 (2) an amine which contains an amino group having at least one active hydrogen atom, and (3) an aldehyde, wherein the respective molar ratio of reactants (1), (2) and (3) is 1:0.1–10:0.1–10.

3. The method according to claim 1, wherein about 100 to 200 g of magnesium silicate are employed per equivalent of water-soluble amine in the diluted crude Mannich condensation product.

4. The method according to claim 1, wherein about 35 to 85 g of water are employed per equivalent of water-soluble amine in the diluted crude Mannich condensation product.

5. The method according to claim 1, wherein the filter aid is present at a concentration of about 0.2 to 1.5%, based on the diluted crude Mannich condensation product.

6. The method according to claim 1, wherein the filter aid is diatomaceous earth.

7. The method according to claim 1, wherein the filtering is carried out at a temperature in the range of about 40° C. to 95° C.

8. The method according to claim 1, wherein the filtrate containing the Mannich condensation product has less than about 0.04 mEq/g of water-soluble amine.

9. The method according to claim 1, wherein about 0.1 to 2%, based on the diluted crude Mannich condensation product, of a filter aid is used when the particle size distribution of the magnesium silicate is such that the average particle size is equal to or greater than about 50 microns.

* * * * *